US009023107B2

(12) United States Patent
Muhanna

(10) Patent No.: US 9,023,107 B2
(45) Date of Patent: May 5, 2015

(54) VERTEBRAL BODY REPLACEMENT

(75) Inventor: Nabil L. Muhanna, Gainesville, GA (US)

(73) Assignee: Spinal USA, Inc., Parsippany, NJ (US)

( * ) Notice: Subject to any disclaimer, the term of this patent is extended or adjusted under 35 U.S.C. 154(b) by 950 days.

(21) Appl. No.: 12/613,865

(22) Filed: Nov. 6, 2009

(65) Prior Publication Data
US 2010/0082106 A1 Apr. 1, 2010

Related U.S. Application Data

(63) Continuation-in-part of application No. 11/937,242, filed on Nov. 8, 2007, now Pat. No. 8,920,502.

(60) Provisional application No. 61/122,519, filed on Dec. 15, 2008, provisional application No. 60/864,857, filed on Nov. 8, 2006.

(51) Int. Cl.
| A61F 2/44 | (2006.01) |
| A61F 2/46 | (2006.01) |
| A61F 2/28 | (2006.01) |
| A61F 2/30 | (2006.01) |

(52) U.S. Cl.
CPC .............. *A61F 2/442* (2013.01); *A61F 2/4465* (2013.01); *A61F 2/447* (2013.01); *A61F 2/4611* (2013.01); *A61F 2002/2835* (2013.01); *A61F 2002/30495* (2013.01); *A61F 2002/3055* (2013.01); *A61F 2002/30598* (2013.01); *A61F 2002/30601* (2013.01); *A61F 2002/30733* (2013.01); *A61F 2002/30818* (2013.01); *A61F 2220/0025* (2013.01); *A61F 2310/00017* (2013.01); *A61F 2310/00023* (2013.01); *A61F 2310/00029* (2013.01)

(58) Field of Classification Search
USPC .......................................... 623/17.11–17.16
See application file for complete search history.

(56) References Cited

U.S. PATENT DOCUMENTS

| 4,657,550 | A | | 4/1987 | Daher |
| 5,236,460 | A | | 8/1993 | Barber |
| 5,290,312 | A | | 3/1994 | Kojimoto et al. |
| 5,306,310 | A | | 4/1994 | Siebels |
| 5,702,455 | A | | 12/1997 | Saggar |
| 5,980,522 | A | * | 11/1999 | Koros et al. ................. 623/17.11 |
| 6,176,881 | B1 | * | 1/2001 | Schar et al. ................. 623/17.11 |
| 6,352,556 | B1 | | 3/2002 | Kretschmer et al. |

(Continued)

OTHER PUBLICATIONS

The ongoing prosecution history of U.S. Appl. No. 11/937,242, filed Nov. 8, 2007, including without limitation Office Actions, Amendments, Remarks, and any other potentially relevant documents.

*Primary Examiner* — Matthew Lawson
(74) *Attorney, Agent, or Firm* — Knobbe, Martens, Olson & Bear, LLP.

(57) ABSTRACT

This invention concerns a vertebral body replacement element to be inserted into an intervertebral space, thus supporting the spinal column of a patient. The vertebral body replacement element has a hollow upper member and a hollow lower member, with the upper member and lower member engaging in a telescopic manner and establishing a cavity between the two members when assembled. Spacers may be inserted in the cavity to lengthen the vertebral body replacement element. The present invention further concerns a system and method for expanding and distracting a vertebral body replacement element into and within the spinal column of a patient.

15 Claims, 3 Drawing Sheets

(56) References Cited

U.S. PATENT DOCUMENTS

| | | |
|---|---|---|
| 6,524,341 B2 | 2/2003 | Lang et al. |
| 6,758,862 B2 | 7/2004 | Berry et al. |
| 6,866,682 B1 | 3/2005 | An et al. |
| 6,908,485 B2 | 6/2005 | Crozet et al. |
| 6,964,686 B2 | 11/2005 | Gordon |
| 6,991,653 B2 | 1/2006 | White et al. |
| 7,309,358 B2 | 12/2007 | Berry et al. |
| 7,458,988 B2 | 12/2008 | Trieu et al. |
| 2001/0056302 A1 | 12/2001 | Boyer et al. |
| 2002/0128716 A1 | 9/2002 | Cohen et al. |
| 2003/0074064 A1* | 4/2003 | Gerbec et al. .............. 623/16.11 |
| 2004/0172129 A1 | 9/2004 | Schafer et al. |
| 2004/0181283 A1 | 9/2004 | Boyer et al. |
| 2004/0267364 A1 | 12/2004 | Carli et al. |
| 2005/0096744 A1 | 5/2005 | Trieu et al. |
| 2005/0113924 A1 | 5/2005 | Buttermann |
| 2005/0187634 A1 | 8/2005 | Berry |
| 2005/0216084 A1 | 9/2005 | Fleischmann et al. |
| 2006/0058877 A1 | 3/2006 | Gutlin et al. |
| 2006/0058879 A1* | 3/2006 | Metz-Stavenhagen .... 623/17.15 |
| 2006/0129241 A1 | 6/2006 | Boyer et al. |
| 2006/0200244 A1 | 9/2006 | Assaker |
| 2006/0241762 A1 | 10/2006 | Kraus |
| 2006/0293755 A1 | 12/2006 | Linder et al. |
| 2007/0129805 A1 | 6/2007 | Braddock et al. |
| 2007/0129806 A1 | 6/2007 | Harms et al. |
| 2007/0255410 A1 | 11/2007 | Dickson et al. |
| 2007/0270957 A1 | 11/2007 | Heinz |
| 2007/0288092 A1 | 12/2007 | Bambakidis |
| 2008/0058931 A1 | 3/2008 | White et al. |
| 2008/0138083 A1 | 6/2008 | Lee et al. |
| 2009/0005874 A1 | 1/2009 | Fleischmann et al. |
| 2009/0048673 A1 | 2/2009 | Le Huec |
| 2009/0112320 A1 | 4/2009 | Kraus |
| 2009/0112324 A1 | 4/2009 | Refai et al. |
| 2009/0112325 A1 | 4/2009 | Refai et al. |
| 2009/0138089 A1 | 5/2009 | Doubler et al. |

* cited by examiner

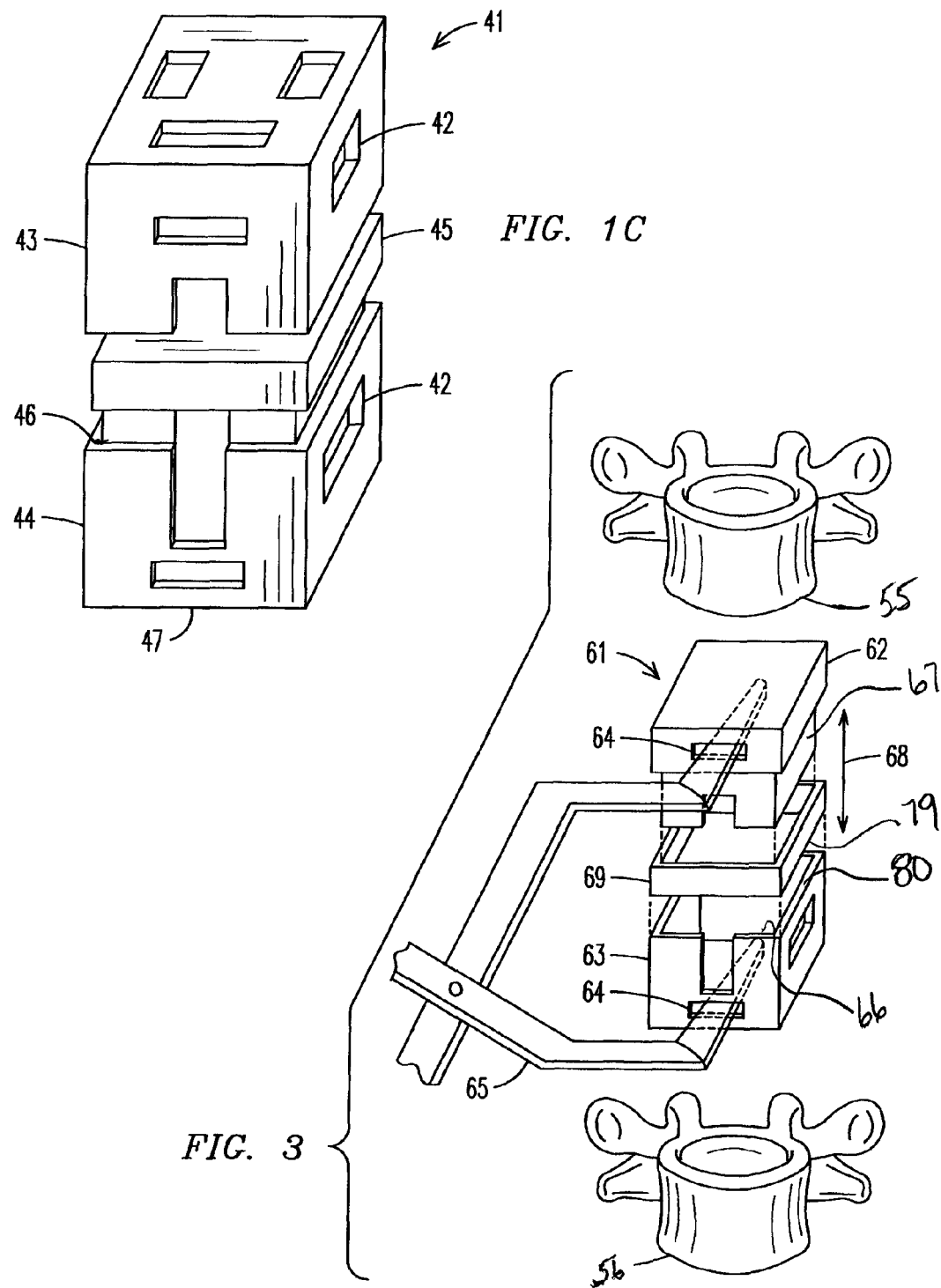

VERTEBRAL BODY REPLACEMENT

CROSS-REFERENCE TO RELATED APPLICATION

This application claims the benefit of U.S. Provisional Patent Application Ser. No. 61/122,519, filed Dec. 15, 2008; and this application is a continuation-in-part patent application of U.S. patent application Ser. No. 11/937,242, filed on Nov. 8, 2007 now U.S. Pat. No. 8,920,502, which application claims the benefit of U.S. Provisional Patent Application Ser. No. 60/864,857, filed Nov. 8, 2006. The specifications and drawings of Ser. No. 11/937,242 and 60/864,857 are herein incorporated by reference.

FIELD OF THE INVENTION

The present invention generally relates to a vertebral body replacement to be inserted into an intervertebral space, thereby supporting the spinal column of a patient. The present invention further relates to a system and method for expanding and distracting a vertebral body replacement element into and within the spinal column of a patient.

BACKGROUND OF THE INVENTION

Back pain is one of the most significant problems facing the workforce in the United States today, is a leading cause of sickness-related absenteeism, and the main cause of disability for people between the ages of 19 and 45. Back pain can occur from pinching or irritating a spinal nerve, compression of the spine, vertebral shifting relative to the spinal cord axis, and formation of bone spurs. The most common cause of disabling back pain, however, generally stems from trauma to a vertebral disc, such as from mechanical shock, stress, tumors, or degenerative diseases. In many cases, the disc can become permanently damaged or degenerated, such that the preferred treatment necessitates partial or total excision and replacement of the damaged disc.

Traumatic injury to a vertebral disc that is not removed frequently can promote scar tissue formation. Such scar tissue typically is thicker than the healthy tissue, such that the disc continues to progressively degenerate, lose water content, and can stiffen and become significantly less effective as a shock absorber. Eventually, the disc can deform, herniate, or collapse, eliminating the flexibility of the spinal column, and potentially leading to further degeneration or damage to other vertebral discs of the spinal column. At such a point, the only option is for the damaged disc to be partially or completely removed.

When the disc is partially or completely removed, generally it is necessary to replace the excised material to prevent direct contact between the bony surfaces of the adjacent vertebrate on either side of the removed disc. For example, U.S. Pat. No. 6,824,565 of Muhanna discloses a vertebral spacer that is inserted between adjacent vertebrate to provide restorative force and function as a shock absorber between the adjacent vertebrate. Another alternative approach has been to insert a "cage" that can maintain a space occupied by the removed disc to prevent the vertebrate from collapsing and impinging upon the nerve roots of the spine. Still further, spinal fusion has been used to restrict motion and stabilize patients' spines by fusing adjacent vertebrate together. This generally can reduce mechanical back pain by preventing the now immobile vertebrate from impinging on a spinal nerve; however, such stability and pain reduction generally is created at the expense of spinal flexibility and motion. In addition, many conventional techniques for disc repair and replacement can be limited in terms of their size or configuration and thus generally are not designed to accommodate variations in size of the gap resulting from the excising of the vertebral disc material. Further, conventional techniques often cannot accommodate expansion or growth of the spine, frequently requiring replacement of the vertebral spacers with other, different size spacers.

Accordingly, it can be seen that a need exists for a vertebral body replacement and system and method of implanting such a vertebral body replacement that addresses the forgoing related and unrelated problems in the art.

BRIEF DESCRIPTION OF THE DRAWINGS

FIGS. 1A-1C are perspective illustrations of various alternative embodiments of the vertebral body replacement member according to the principles of the present invention.

FIG. 3 is a perspective illustration, illustrating the distraction of the intervetebral body replacement member according to the principles of the present invention positioned between adjacent vertebrate of the patient's spine to enable insertion of a spacer therebetween.

DESCRIPTION OF THE INVENTION

Figure 1A:
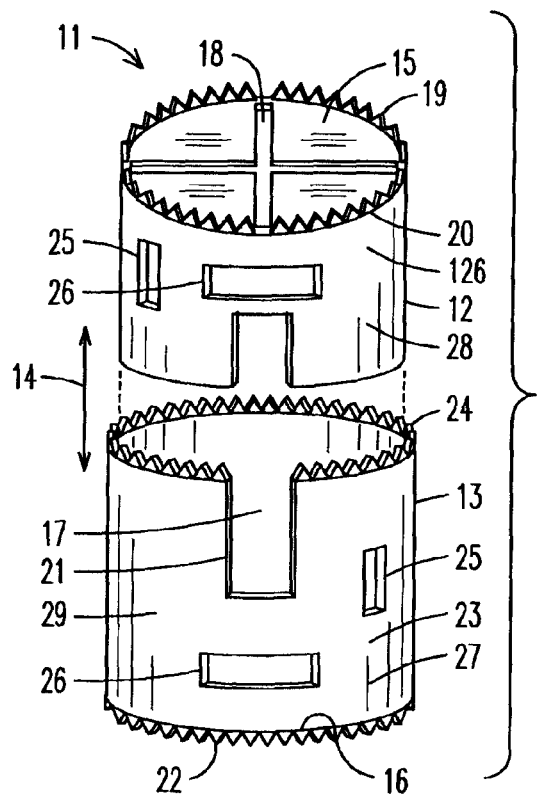
Figure 1B:
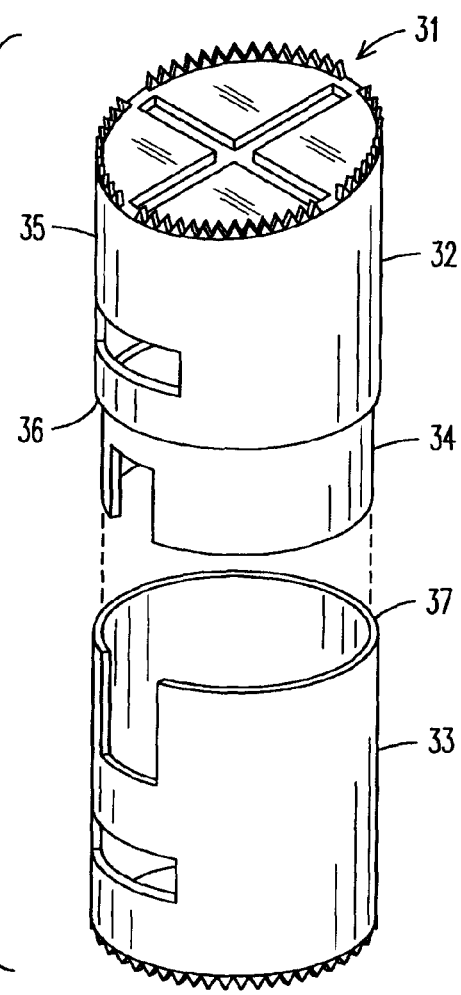

As generally illustrated in FIGS. 1A-1C, the disclosed apparatus is directed to a vertebral body replacement member or elements for insertion into an intervertebral space or gap between vertebrae of a patient's spine to replace substantially all of a vertebral disc or vertebrae that has been excised or removed due to damage or degeneration of the disc. The vertebral body replacement member generally is useful to replace a vertebral disc that has degenerated due to traumatic injury, vertebral displacement, disease (i.e., autoimmune disease, rheumatoid arthritis, etc.), or any other pathological condition of the spinal column that may injure or shift the intervetebral discs. The vertebral body replacement member provides support to the adjacent vertebrae of the patient's spine to help maintain the separation between the vertebrae, while also preserving the natural curvature of the spine and further enabling regenerative bone growth and adjustment of the intervertebral spacing between the adjacent vertebrae to accommodate growth or expansion therebetween.

Figure 2:
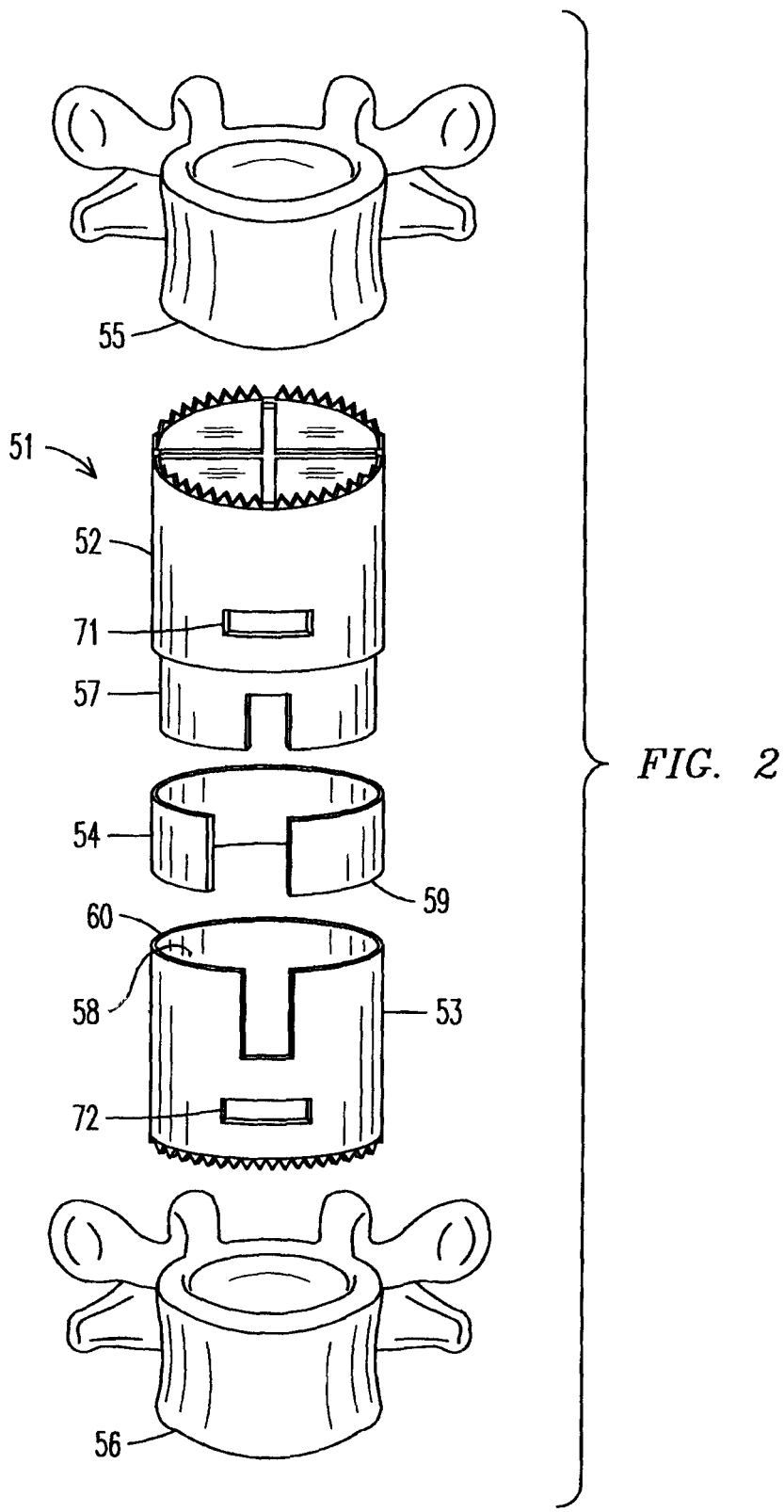
FIG. 2 is an exploded perspective illustrating the installation of the vertebral body replacement member such as illustrated in FIG. 1A or 1B within the spinal column of a patient.

It is generally contemplated that the vertebral body replacement member can be made from any bio-compatible or physically inert material or combination of such materials having the mechanical strength capable of maintaining the intervetebral space between adjacent vertebrae, as indicated in FIGS. 2 and 3, without impinging upon nerves and/or restricting movement and further bone growth or regeneration of the spinal column discs adjacent the intervetebral space in which the disclosed apparatus is mounted. Examples of such materials can include bone, such as bone sections from a femur or other bones of the patient or from donors, metal materials such as titanium, titanium alloys, stainless steel, chrome, cobalt, and other, similar materials, as well as various polymeric materials such as methyl methacrylate (MMA), urethane, polyacetal material, reinforced polymers such as carbon fiber or polyether keytone, polycarbonates, polypropylene, polyamides, and silicone based polymers as generally understood in the art.

As illustrated in FIGS. 1A-1C, the vertebral body replacement member generally includes a telescoping construction, including an upper section and a lower section. Turning now to FIG. 1A, an upper section 12 and a lower section 13 of the vertebral body replacement member 11 engage or interface via a sliding joint which allows relative linear motion in the direction of an axis of linear motion 14. Assembly, adjustment, and removal of the vertebral body replacement member 11 is enhanced with the sliding joint because the sections advantageously move more freely than with other attachment or interfacing means. While alternate attachment or interfacing means may be available, an acceptable alternate does not include a threaded means. The upper section 12 and the lower section 13 can be formed in various configurations or cross sections. Such configurations generally include a cylindrical configuration, having a substantially circular cross section as illustrated in FIGS. 1A and 2; a generally cylindrical configuration with a substantially oval cross-section as illustrated in FIG. 1B; or in square or rectangular configurations as generally illustrated in FIGS. 1C and 3. Among other functions, the non-circular embodiments have the added benefit of restricting longitudinal rotation relative to the axis of linear motion 14 between the upper section 12 and the lower section 13. An alternate means of restricting longitudinal rotation between the upper and lower sections from those disclosed in FIGS. 1B and 1C would be a key and keyway interface (not illustrated). In some applications, restriction of longitudinal rotation is desired and is accomplished by the non-circular alternate embodiments. The circular configuration is advantageous in that although longitudinal rotation is not required, it is possible, while providing relative linear motion of the upper section 12 and the lower section 13. Further, as illustrated in FIG. 1A, with a top surface 15 and a bottom surface 16 angled or contoured as discussed below, restricting longitudinal rotation of the upper section 12 and the lower section 13 is desired. Each of the upper section 12 and the lower section 13 further generally includes an open-ended body formed from a bio-compatible or physically inert material as discussed above, and one of the sections, for example the upper section 12, will be formed with at least a portion of its body having a slightly smaller diameter or cross-sectional area than the lower section so as to telescope into and out of the open upper end of the lower section 13 as indicated in FIGS. 1A-1C. It will, however, also be understood that the upper section 12 and the lower section 13 can be formed with the lower section 13 telescoping into and out of the upper section 12 as needed or desired.

The open ended structures of the upper section 12 and the lower section 13 further generally define a space or cavity 17 within the vertebral body replacement member 11 as the two sections 12, 13 are brought together. The upper section 12 generally includes a substantially flat top surface 15 that further can include channels 17 or openings formed therein, and, as illustrated in FIGS. 1A and 1B, further can include a series of teeth or serrations 19 formed about the side edge 20 of the top surface 19 of the upper section 12 to help secure it against an adjacent upper vertebrae (not illustrated). The lower section 13 typically has a similar construction, with an open upper end, a closed, substantially flat bottom surface 16, and further generally includes slots 21 or openings formed in its bottom or base plate. The lower section 13 also can include series of teeth or serrations 22 formed about the side 23 of its lower or bottom base plate to help engage and fix the lower section 13 to the lower vertebrae (not illustrated) of the patient's spine in which it is mounted. Additionally, an upper portion of the lower section 13 may also include teeth or serrations 24, further aiding in support of the component 11 to the vertebrae. The top surface 15 and the bottom surface 16 of the upper section 12 and the lower section 13, respectively, additionally can be angled or contoured as needed to substantially match the contour of the adjacent upper and lower vertebrae on which the sections 12, 13 are mounted or engaged.

Openings 25 are formed in top 126 and bottom 27 portions of the upper section 12 and the lower section 13, respectively, of the vertebral body replacement member 11 and provide areas or points of access for bone to grow and expand into the surrounding tissue about the patient's spine to help further secure the vertebral body replacement member 11 within the patient's spine and to foster or facilitate regeneration and additional bone growth. As illustrated in FIG. 1C, growth openings 42 are also formed in the side walls thereof. The telescoping construction of the vertebral body replacement member 11 further enables the vertebral replacement member 11 to expand or extend as needed to accommodate such additional or regenerative bone growth and to enable further adjustment of the spacing provided by the vertebral body replacement member 11 as needed to fit the intervetebral space created by the excising or removal of part or the entirety of the damaged vertebral disc.

As further illustrated in FIG. 1A, the upper section 12 and the lower section 13 each generally include a large slotted opening 26 formed through the side wall or walls of the upper section 12 and the lower section 13 of the vertebral body replacement member 11. This opening 26 enables the insertion and packing of bone material within the cavity 17 defined between the upper section 12 and the lower section 13 of the vertebral body replacement 11 member after implantation or placement of the vertebral body replacement member 11 within the patient's spine. Such implanted bone material can then fuse to and grow with the existing remaining vertebrae of the patient, expanding out through the openings 26 formed in the top 15, bottom 16, and upper side wall 28 of the upper section 12 and lower side wall 29 of the lower section 13, respectively, of the vertebral body replacement member 11 and into contact with the adjacent upper and lower vertebrae and the tissue surrounding the patient's spine.

Alternate embodiments of the vertebral body replacement member are illustrated in FIGS. 1B and 1C. FIG. 1B illustrates a vertebral body replacement member 31 having an upper section 32 and a lower section 33. The upper section 32 and the lower section 33 assemble such that the two sections 32, 33 fit together in a telescopic fashion. The upper section 32 and the lower section 33 are oval in cross section, thus preventing relative rotation between the two sections 32, 33. In this embodiment, the upper section 32 has a lower portion 34 with a reduced diameter from an upper portion 35. A lip 36 is formed at the interface of the upper portion 35 and the lower portion 34. When the upper section 32 and the lower section 33 are assembled, the lip 36 rests on, or comes into contact with, a rim 37 of the lower section 33 and establishes a length of the vertebral body replacement member 31. Illustrated in FIG. 1C, a vertebral body replacement member 41 is shown having an upper section 43 and a lower section 44 with the upper section 43 and lower section 44 being square, or rectangular, in cross section. A spacer 45 fits between the upper section 43 and the lower section 44 and establishes, among other things, a length of the vertebral replacement body member 41. The spacer 45 may also increase the overall rigidity of the component 11, help absorb shock during use, reduce component 41 wear, and reduce the amount of packing material necessary. When assembled, the spacer 45 may be contained within a cavity 46 and rest on a base 47 of the lower section 44.

Still further, as illustrated in FIG. 3, the upper section 62 and the lower section 63 of the vertebral body replacement member 61 further generally will include a distraction slot 64 or similar opening for receiving a distracter instrument 65 or tool therein. Alignment of the distraction instrument 65 or tool with the distraction slot 64 is preserved because of the restriction of relative longitudinal rotation between the upper section and lower section in the non-circular embodiments (and the circular embodiment with keyways or other restrictive rotational restraints). The ends of the distracter instrument 65 will be introduced into the distraction slots 64 formed in the upper section 62 and the lower section 63 for placement of the vertebral body replacement member 61 within the vertebral space or excised area between the adjacent vertebrae 55, 56 and thereafter expanding the sections as needed by causing the upper section 62 and the lower section 63 to telescope or move outwardly in a direction of travel 68 away from each other so as to expand the intervertebral body replacement member 61 as needed to fill the intervertebral space.

In addition, as illustrated in FIGS. 2 and 3, one or more spacers 69 (spacers are seen as 54 in FIG. 2) also can be mounted between the upper and lower sections of the vertebral body replacement member as needed. Turning now to FIG. 2, the spacers 54 generally will be made from the same or a compatible material as the upper section 52 and the lower section 53 of the vertebral body replacement member 51 and typically will be of a similar configuration and/or size as the upper section 52 and the lower section 53 so as to fit therebetween without substantially overlapping the side edges of the upper section 52 and the lower section 53 and, provide a more mechanically robust and rugged structure due to the superior load carrying abilities of a nested structure in compression having a large load bearing surface. For example, as illustrated in FIGS. 2 and 3, the upper section 52, 62 of the vertebral body replacement member 51, 61 can include a bottom portion 57, 67 formed with a reduced area or diameter that is adapted to be received and telescope into the open upper end 58, 66 of the lower section 53, 63. The spacers 54, 69 can be of a similar size and configuration as the upper section 52, 62 and the lower section 53, 63 so as to fit over this recessed portion 57, 67 of the upper section 52, 62. The spacers 54, 69 also can be provided with teeth (not shown) as needed to help secure the spacers in place within the intervertebral space, between the adjacent vertebrae 55, 56. The spacer 54, 69 may be configured as a hollow band (for example, but not limited to, a cylindrical ring or rectangular band), having an inner diameter or inside perimeter that is similar to the diameter or perimeter of the recessed portion 57, 67. The terms "ring" and "band" are used interchangeably in this disclosure. The ring shaped spacer 54, 69 may also be a split ring (or split band) to facilitate assembly. As a ring, the spacer 54, 69 is free to slide telescopically along the recessed portion 57, 67 so when assembled, the lower surface 59, 79 of the spacer 54, 69 will rest against the upper rim 60, 80 of the lower section 53, 63 thereby establishing the length of the vertebral body replacement member 51, 61.

The spacers 54, 69 typically will be inserted as needed after implantation of the vertebral body replacement member 51, 61 within the intervetebral space, by engagement of the upper section 52, 62 and the lower section 53, 63 of the vertebral body replacement 51, 61 member by the distraction tool (see FIG. 3) and expansion thereof, so as to create a gap in which the spacer(s) 54, 69 can be inserted. Thereafter, as the distraction instrument is closed, the upper section 52, 62 and the lower section 53, 63 of the vertebral body replacement member 51, 61 will be brought together, sealing into engagement with each other and with any spacers 54, 69 contained therebetween. Thereafter, the distraction tool or instrument can be removed and the surgical opening in the patient's back closed. Still further, if additional spacers 54, 69 are needed, the distraction tool can be engaged with the slots in an upper slot 71, 64 and a lower slot 72, 64 and the upper section 52, 62 and the lower section 53, 63 further separated to enable implantation of a additional spacers 54, 69 as needed.

The present invention thus provides a simple device, typically made from a single, biocompatible material with minimal parts and generally utilizing only a minimal presences of screws, if at all, or similar fasteners to attach the upper and lower sections of the vertebral body replacement member to the adjacent vertebrate of the patient. The vertebral body replacement member further is radiolucent and expandable, and any distraction required is done by distracting the device internally through the engagement of the distraction instrument with the slotted openings in the upper and lower sections thereof, such that there is no distraction or engagement of screws that could damage bone. The growth openings formed in the top, bottom and side walls of the upper and lower sections, respectively, further enable bone growth out of the vertebral body replacement member and into the surrounding bone and tissue to help promote healing and more natural freedom of movement, while maintaining the intervetebral space and preventing collapse of the patient's spine.

It will be understood by those skilled in the art that while the foregoing has been described with reference to preferred embodiments and features, various modifications, variations, changes and additions can be made thereto without departing from the spirit and scope of the invention.

What is claimed:

1. An adjustable vertebral body replacement assembly for placement in an intervertebral space between adjacent vertebrae, comprising:
    a first component defining a body having a first end configured to contact a proximal vertebral body and an open second end distal to the first end, the open second end having a second end rim at a distalmost edge of the open second end;
    a second component defining a body having a third end configured to contact a distal vertebral body and a fourth end from which extends a protrusion configured to pass through the second end rim, the protrusion slidable in at least two directions within said open second end; and
    a removable spacer having a first spacer length and configured to partially surround and slidably engage said protrusion;
    wherein when said protrusion is within the open second end and the removable spacer is slidably engaged with said protrusion, the removable spacer is configured to be disposed on an exterior surface of said protrusion and configured to contact the distalmost edge of the open second end and a proximal edge of the fourth end such that the removable spacer is configured to be positioned entirely between the distalmost edge of the open second end and the proximal edge of the fourth end.

2. The adjustable vertebral body replacement assembly as claimed in claim 1, wherein the spacer further comprises a central opening having an inner surface that is configured to contact an outer surface of said protrusion.

3. The adjustable vertebral body replacement assembly as claimed in claim 2, further comprising an outer surface of the body of the second component and a lip formed on the fourth end of the second component between the protrusion and the outer surface of the body of the second component.

4. The adjustable vertebral body replacement assembly as claimed in claim 3, wherein when said protrusion is within the open second end and the removable spacer is slidably engaged with said protrusion, the removable spacer is further configured to nest between the second end rim and the lip formed on the fourth end of the second component.

5. The adjustable vertebral body replacement assembly as claimed in claim 1, wherein the first end and third end are flat and configured to contact adjacent vertebrae.

6. The adjustable vertebral body replacement assembly as claimed in claim 1, wherein the first component and the second component further comprise a plurality of openings or channels.

7. The adjustable vertebral body replacement assembly as claimed in claim 1, wherein the first end and the third end include a series of teeth or serrations to secure the first and second components to adjacent vertebrae.

8. The adjustable vertebral body replacement assembly as claimed in claim 1, wherein the first component comprises a keyway and the protrusion comprises a key sized to fit within the keyway to resist relative rotation between the first component and the second component.

9. The adjustable vertebral body replacement assembly as claimed in claim 1, wherein the first component and the second component each have a distraction slot for receiving a first end and a second end of a distracter instrument.

10. The adjustable vertebral body replacement assembly as claimed in claim 1, wherein a cross section of the first component and a cross section of the second component are circular.

11. The adjustable vertebral body replacement member as claimed in claim 1, wherein a cross section of the first component and a cross section of the second component are rectangular or square.

12. The adjustable vertebral body replacement member as claimed in claim 1, wherein the vertebral body replacement member is adjustable by sliding the first component telescopically with respect to the second component.

13. The adjustable vertebral body replacement member as claimed in claim 1, wherein the protrusion is sized to create a sliding joint with no relative rotation between the first component and the second component.

14. An adjustable vertebral body replacement assembly for placement in an intervertebral space between adjacent vertebrae, comprising:

a first component defining a body having a first end configured to contact a proximal vertebral body and an open second end distal to the first end, the open second end having a second end rim at a distal edge of the open second end;

a second component defining a body having a third end configured to contact a distal vertebral body and a fourth end from which extends a protrusion configured to pass through the second end rim, the protrusion slidable in at least two directions within said open second end;

a removable spacer having a first spacer length and configured to partially surround and slidably engage said protrusion;

at least one additional removable spacer to thereby establish a plurality of spacers, each spacer having a spacer length and configured to partially surround and slidably engage said protrusion; and wherein when said protrusion is within the open second end and the removable spacer is slidably engaged with said protrusion, the removable spacer is configured to contact a distal facing surface of the second end rim.

15. An adjustable vertebral body replacement assembly for placement in an intervertebral space between adjacent vertebrae, comprising:

a first component defining a body having a first end configured to contact a proximal vertebral body and an open second end distal to the first end, the open second end having a second end rim at a distal edge of the open second end;

a second component defining a body having a third end configured to contact a distal vertebral body and a fourth end from which extends a protrusion configured to pass through the second end rim, the protrusion slidable in at least two directions within said open second end; and a removable spacer having a first spacer length and configured to partially surround and slidably engage said protrusion;

wherein when said protrusion is within the open second end and the removable spacer is slidably engaged with said protrusion, the removable spacer is configured to contact a distal facing surface of the second end rim;

wherein a vertebral body length of the vertebral body replacement assembly is adjusted by replacing said removable spacer having the first spacer length with a removable spacer having a second spacer length, and wherein a change in said vertebral body length is approximately equal to a difference between said first spacer length and said second spacer length.

* * * * *

UNITED STATES PATENT AND TRADEMARK OFFICE
CERTIFICATE OF CORRECTION

| | | |
|---|---|---|
| PATENT NO. | : 9,023,107 B2 | Page 1 of 1 |
| APPLICATION NO. | : 12/613865 | |
| DATED | : May 5, 2015 | |
| INVENTOR(S) | : Nabil L. Muhanna | |

It is certified that error appears in the above-identified patent and that said Letters Patent is hereby corrected as shown below:

In the specification
In column 1, line 53, change "bony" to --boney--.
In column 2, line 23, change "intervetebral" to --intervertebral--.
In column 2, line 41, change "intervetebral" to --intervertebral--.
In column 2, line 52, change "intervetebral" to --intervertebral--.
In column 2, line 55, change "intervetebral" to --intervertebral--.
In column 4, line 19, change "intervetebral" to --intervertebral--.
In column 5, line 58, change "intervetebral" to --intervertebral--.
In column 6, line 23, change "intervetebral" to --intervertebral--.

Signed and Sealed this
Seventeenth Day of May, 2016

Michelle K. Lee
*Director of the United States Patent and Trademark Office*